United States Patent
Loi et al.

(10) Patent No.: US 10,132,934 B2
(45) Date of Patent: Nov. 20, 2018

(54) INTEGRATED DETECTION DEVICE, IN PARTICULAR DETECTOR OF PARTICLES SUCH AS PARTICULATES OR ALPHA PARTICLES

(71) Applicant: STMICROELECTRONICS S.R.L., Agrate Brianza (IT)

(72) Inventors: Sara Loi, Cagliari (IT); Alberto Pagani, Nova Milanese (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 401 days.

(21) Appl. No.: 14/748,961

(22) Filed: Jun. 24, 2015

(65) Prior Publication Data
US 2016/0077218 A1 Mar. 17, 2016

(30) Foreign Application Priority Data

Sep. 17, 2014 (IT) .............................. TO2014A0734

(51) Int. Cl.
*G01T 1/178* (2006.01)
*G01N 15/02* (2006.01)
(Continued)

(52) U.S. Cl.
CPC ............. *G01T 1/178* (2013.01); *G01N 15/02* (2013.01); *G01N 15/06* (2013.01); *G01T 1/244* (2013.01);
(Continued)

(58) Field of Classification Search
CPC ....... G01T 1/178; G01T 1/244; G01T 1/2928; G01N 15/06; G01N 15/02; G01N 15/0205;
(Continued)

(56) References Cited

U.S. PATENT DOCUMENTS

| 4,210,923 A | 7/1980 | North et al. |
| 4,668,374 A * | 5/1987 | Bhagat ............... G01N 27/4071 |
| | | 204/412 |

(Continued)

FOREIGN PATENT DOCUMENTS

| CN | 102985644 A | 3/2013 |
| CN | 103226125 A | 7/2013 |

(Continued)

OTHER PUBLICATIONS

Grimm Aerosol Technik GMBH & Co., KG—Portable Laser Aerosol Spectrometer and Dust Monitor, Model No. 1.108/1.109, 81 pp, 2010, Germany. http://www.wmo-gaw-wcc-aerosol-physics.org/files/OPC-Grimm-model--1.108-and-1.109.pdf.

(Continued)

*Primary Examiner* — Marcus Taningco
*Assistant Examiner* — Gisselle Gutierrez
(74) *Attorney, Agent, or Firm* — Slater Matsil, LLP

(57) ABSTRACT

A detection device is formed in a body of semiconductor material having a first face, a second face, and a cavity. A detection area formed in the cavity, and a gas pump is integrated in the body and configured to force movement of gas towards the detection area. A detection system of an optical type or a detector of alpha particles is arranged at least in part in the detection area.

38 Claims, 10 Drawing Sheets

(51) Int. Cl.
*G01N 15/06* (2006.01)
*G01T 1/24* (2006.01)
*G01T 1/29* (2006.01)
*G01N 15/00* (2006.01)
*G01N 15/10* (2006.01)
*G01N 1/22* (2006.01)
*F04B 19/06* (2006.01)
*F04B 37/00* (2006.01)

(52) U.S. Cl.
CPC ............ *G01T 1/2928* (2013.01); *F04B 19/06* (2013.01); *F04B 37/00* (2013.01); *G01N 15/0205* (2013.01); *G01N 15/10* (2013.01); *G01N 2001/2276* (2013.01); *G01N 2015/035* (2013.01)

(58) Field of Classification Search
CPC ..... G01N 2015/035; G01N 2001/2276; G01N 15/10; F04B 37/00; F04B 19/06
USPC .................................................. 250/370.02
See application file for complete search history.

(56) References Cited

U.S. PATENT DOCUMENTS

| | | | |
|---|---|---|---|
| 5,184,019 A * | 2/1993 | MacArthur | G01T 1/178 250/380 |
| 5,191,394 A | 3/1993 | Saia et al. | |
| 6,225,633 B1 | 5/2001 | Sun et al. | |
| 6,661,035 B2 | 12/2003 | Negro et al. | |
| 6,995,351 B2 | 2/2006 | Curtis et al. | |
| 7,829,904 B2 | 11/2010 | Coffa et al. | |
| 7,847,238 B2 | 12/2010 | Grier | |
| 7,847,360 B2 | 12/2010 | Valvo et al. | |
| 7,980,828 B1 | 7/2011 | Lantz et al. | |
| 8,431,884 B2 | 4/2013 | Grier | |
| 2005/0056780 A1* | 3/2005 | Miller | F03H 1/00 250/288 |
| 2005/0139762 A1* | 6/2005 | Miller | G01N 27/624 250/282 |
| 2006/0280405 A1* | 12/2006 | Gunn, III | G02B 6/1228 385/37 |
| 2007/0176092 A1* | 8/2007 | Miller | G01N 27/624 250/288 |
| 2009/0238723 A1* | 9/2009 | Guharay | G01N 21/658 422/68.1 |
| 2011/0072887 A1* | 3/2011 | Oki | B03C 3/014 73/28.02 |
| 2011/0149461 A1 | 6/2011 | MacDonald et al. | |
| 2013/0031954 A1 | 2/2013 | Yoshioka | |
| 2013/0036793 A1 | 2/2013 | White et al. | |
| 2013/0120749 A1* | 5/2013 | Nicoletti | G01N 15/1484 356/338 |
| 2013/0192989 A1 | 8/2013 | Fix et al. | |
| 2014/0001493 A1 | 1/2014 | Pagani et al. | |
| 2016/0077218 A1 | 3/2016 | Loi et al. | |
| 2017/0038273 A1* | 2/2017 | Krauss | G01N 27/4071 |

FOREIGN PATENT DOCUMENTS

| | | |
|---|---|---|
| CN | 103411864 A | 11/2013 |
| CN | 103868835 A | 6/2014 |
| CN | 205003048 U | 1/2016 |
| EP | 1746414 A3 | 3/2007 |
| JP | 2005156465 A | 6/2005 |
| WO | WO2014006570 A1 | 1/2014 |
| WO | WO2014006570 A8 | 1/2014 |
| WO | WO2014/107504 A1 | 7/2014 |

OTHER PUBLICATIONS

Contec Engineering SRL, DustMonit—Continuous Fine Dust Measuring System, 6 pp, 2009, Italy. http://www.conteng.it/Bollettini/DustMonit_En.pdf.

Wiscombe et al.—Improved Mie Scattering Algorithms, pp. 1505-1509, Applied Optics, vol. 19, No. 9, May 1, 1980.

Liu et al.—Dielectric Materials for Electrowetting-on-dielectric Actuation, 12 pp., Microsyst Technol (2010), Springer-Verlag 2009.

Mekis et al.—A Grating-Coupler-Enabled CMOS Photonics Platform, IEEE Journal of Selected Topics in Quantum Electronics, vol. 17, No. 3, May/Jun. 2011, pp. 597-608.

PEDALA—Particulate Matter Detector Based on Impedance Sensing, Politecnico di Milano, School of Engineering, Thesis, 2012-2013, pp. 82.

Galayko et al.—Clamped-Clamped Beam Micro-Mechanical Resonators in Thick-Film Epitaxial Polysilicon Technology, ESSDERC 2002, European Solid-State Circuits Conference, Firenze, Sep. 24-26, 2002, pp. 447-450.

Kajanto et al.—Photolithographic Fabrication Method of Computer-Generated Holographic Interferograms, Applied Optics, vol. 28, No. 4, Feb. 15, 1989, pp. 778-784.

Muscara et al.—Design and Electro-Optical Characterization of Si-Based Resonant Cavity Light Emitting Devices, IEEE Journal of Quantum Electronics, vol. 47, No. 10, Oct. 2011, pp. 1362-1368.

* cited by examiner

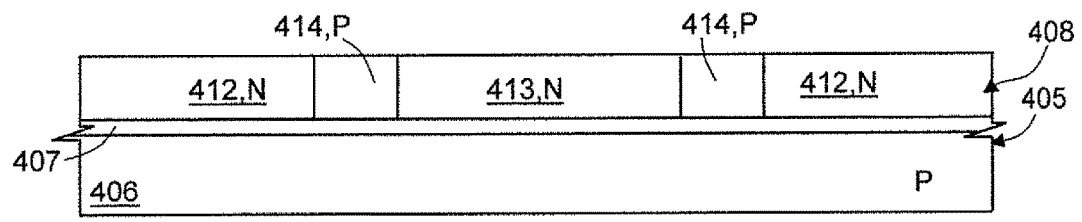
Fig.24A
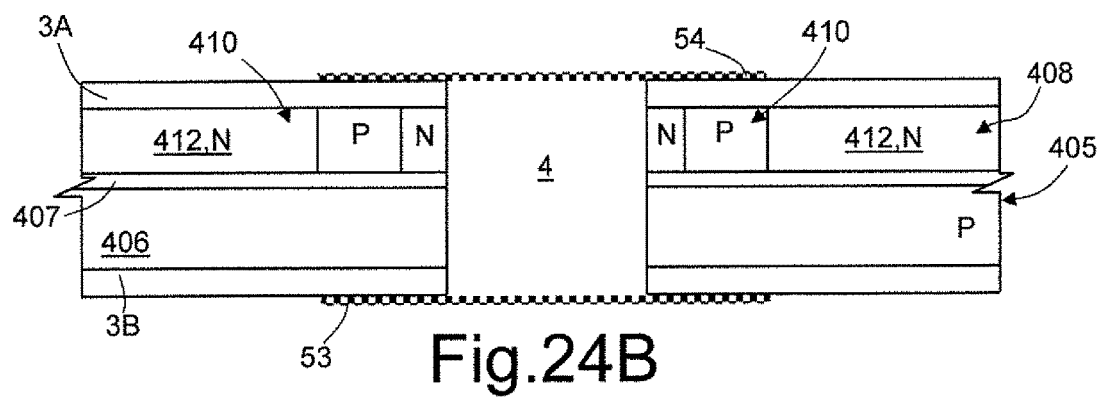
Fig.24B
Fig.25
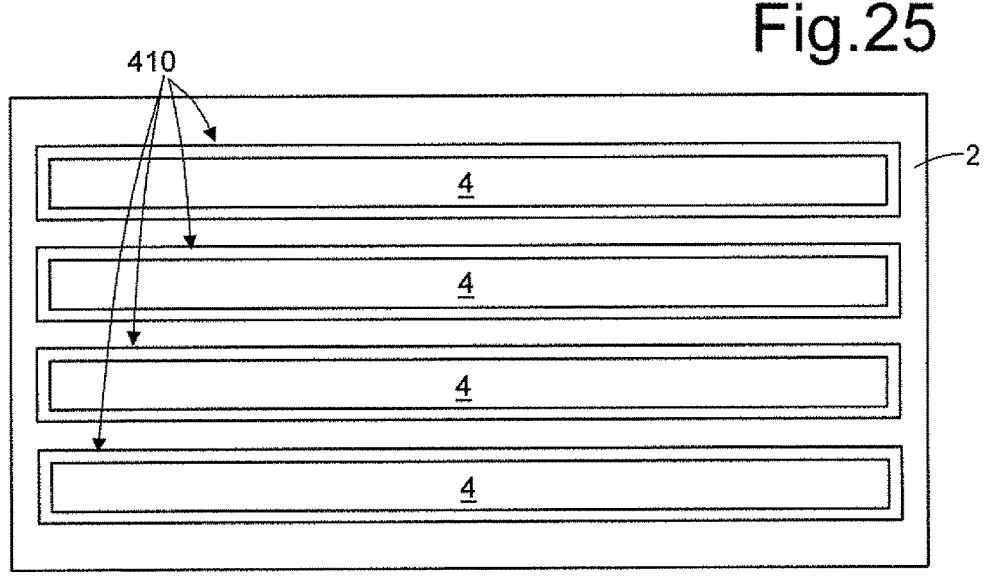

INTEGRATED DETECTION DEVICE, IN PARTICULAR DETECTOR OF PARTICLES SUCH AS PARTICULATES OR ALPHA PARTICLES

FIELD OF THE INVENTION

The present invention relates to an integrated detection device, in particular a detector of particles such as particulates or alpha particles contained in a gas.

BACKGROUND

Particle detectors are known, for example, for detecting particles having a diameter smaller than a preset value. For instance, apparatus are available for measuring particles or particulates PM. Such microscopic particles, which are present in the atmosphere and formed, for example, by dust, smoke, microdrops of aerosol, etc., may present a danger for health and form an environmental risk that affects climate change.

For detecting particles, some apparatus cause an air sample to pass through a channel with a light beam, for example generated by a laser, which, by striking the particles contained in the air, cause scattering thereof. A detector arranged along the path of the scattered light, on the basis of the detected signal, measures the diameter of the particles and counts the number thereof.

For instance, the apparatus "Portable Laser Aerosol Spectrometer and Dust Monitor", Model No. 1.108/1.109, manufactured by Grimm Aerosol Technik GmbH & Co., KG is a portable apparatus including a mirror that concentrates the light in the detector (see also http://www.wmo-gaw-wcc-aerosol-physics.org/files/OPC-Grimm-model--1.108-and-1.109.pdf).

The above system, which detects the particles in their spontaneous concentration, may, however, be improved as regards to the measurement times, which are rather long. Furthermore, the system is hardly applicable with decreasing concentrations to be detected, requires high laser power, and is cumbersome and costly due to the discrete structure.

Another commercial apparatus "DustMonit", manufactured by Contec Engineering Srl, includes a controlled constant-capacity pump that draws in the air through a radial-symmetry probe and conveys it into a chamber, where the transported particles are individually hit by a laser beam. The energy reflected by each particle, proportional to its size, is detected via a photodiode and counted (see also http://www.conteng.it/Bollettini/DustMonit_En.pdf).

The above detector has the disadvantage of detecting the particles one by one, and thus has long measuring times. Furthermore, it introduces an error when particles are aligned along the line joining the detector and the source.

It is thus desirable to have an improved detector that increases the detection efficiency, has high sensitivity as well as short measuring times, small dimensions, and low costs.

SUMMARY

According to the present embodiments of the invention, an integrated detection device of semiconductor material, a process for manufacturing an optical system in a semiconductor body, and a method for detecting particles, is provided.

In practice, the present particle detector includes a semiconductor body integrating a gas pump that accelerates a gas, such as air, and particles contained therein, concentrating them in a body cavity forming a detection area, where the particles are hit by light emitted by a light source to cause light scattering, which is detected via a photodetector. The spatial distribution of the scattered light is correlated to the size of the particles in the air, so that, by appropriate algorithms (Wiscombe W. J., 1980: "Improved Mie scattering algorithms", Appl. Opt., 19, pp. 1505-1509), it is possible to calculate the distribution of the size of the particles contained in the air, starting from Mie's theory regarding scattering of the wavelength of the light, and on the basis of the optical properties of particles (refractive index and absorption coefficient; see, for example, Bohren C. F. and Huffman D. R., 1983, "Absorption and Scattering of Light by Small Particles", John Wiley & Sons, 530 pages). Alternatively, in the case of a detector of alpha particles, emitted, for example, by radon gas, a particle detector is arranged in the detection area, and the gas is accelerated and/or concentrated by the gas pump.

In particular, the gas pump may be of an ionic type where the gas, such as air, is ionized through a structure, for example an ionization grid possibly having tips, and is then attracted towards the detection area by a structure, for example an appropriately biased grid. Alternatively, the gas pump may be of a thermal type with structures configured to create a temperature difference between two extremes of the detection area.

In this way, it is possible to provide both a detector of particulate matter, for example PM10 (particles between 2.5 and 10 micrometers in diameter), PM2.5 (particles less than 2.5 micrometers in diameter), or particulates of even smaller size, and a radon detector.

The semiconductor body integrating the particle detector may accommodate a system of micrometric lenses for adapting the characteristics of the light beam emitted by the optical source, for example, widening it. The lens system may be obtained, for example, by exploiting the hydrophobicity of the materials and/or electrowetting. Alternatively, the lenses may be prefabricated and subsequently put in place.

Alternatively, the beam adjusting system may be any known system used, for example, in the sectors of photonics or MOEMS (Micro-Opto-Electro-Mechanical Systems).

BRIEF DESCRIPTIONS OF THE DRAWINGS

For a better understanding of the embodiments of the invention, the preferred embodiments of the invention are now described purely by way of non-limiting example, with reference to the attached drawings, wherein:

FIGS. 24A and 24B are cross-sections similar to FIG. 23, in successive manufacturing steps; and FIG. 25 is a top plan view of an embodiment of a particle detector.

DETAILED DESCRIPTION

Figure 1:
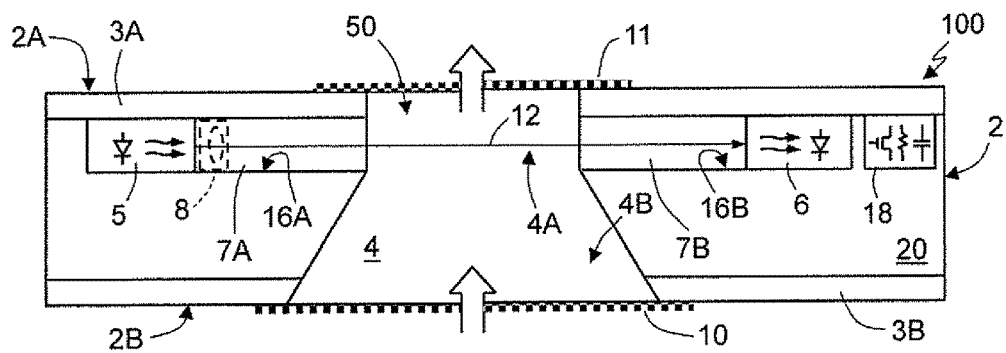
FIG. 1 is a cross-section through an embodiment of a detector of particles such as particulate matter PM10 or PM2.5 or particulates of smaller size.
Figure 2:
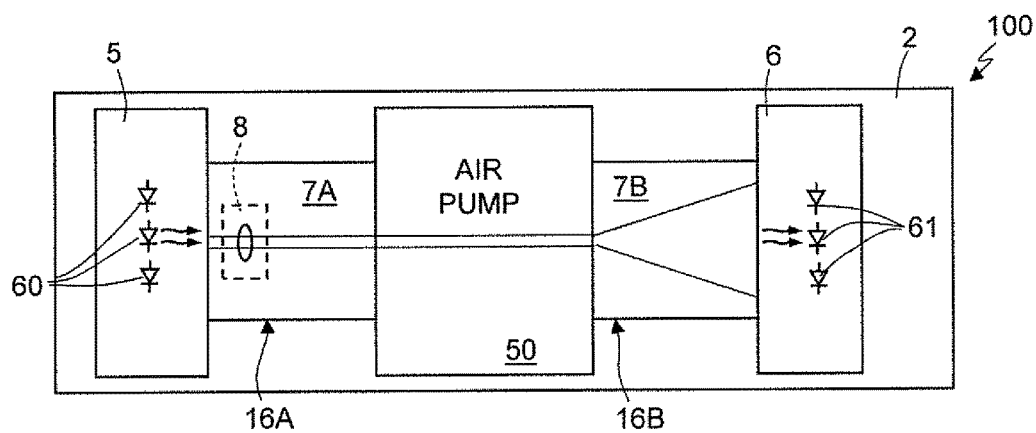
FIG. 2 is a schematic representation of the detector of FIG. 1.

FIGS. 1 and 2 illustrate an embodiment of a particle detector 100 integrated in a body 2 having a first face 2A and a second face 2B. The body 2 may be formed by a substrate 20 of semiconductor material, for example monolithic monocrystalline silicon, covered on one of its major surfaces by a first protective layer 3A and on the other surface by a second protective layer 3B, the protective layers 3A, 3B both being, for example, of insulating material and forming the first and second faces 2A, 2B, respectively.

The body 2 accommodates a sample chamber 4 formed by an opening extending between the two faces 2A and 2B of the body 2. The sample chamber 4 is formed by two mutually contiguous and substantially aligned parts that include a detection area 4A, which extends from the first face 2A, and a concentration area 4B, which extends from the second face 2B of the body 2. In the illustrated example, the detection area 4A has, for example, a generally parallelepipedal shape (see also the top plan view of FIG. 2), and the concentration area 4B has, for example, a frustoconical shape, with its minor base directly adjacent to the detection area 4A and having an area substantially equal to the detection area with its major base facing the second face 2B. Other shapes are, however, possible. For example, the entire sample chamber 4 could be frustoconical or parallelepipedal, without any discontinuity.

The body 2 further integrates an optical detection system including a light source 5, for example a laser-emitting circuit, and a photodetector 6, for example a laser-detecting circuit, which are arranged at the sides of the detection area 4A. In FIG. 1, the light source 5 and the photodetector 6 are arranged on two opposite sides of the detection area 4A. A first transparent region 7A is arranged between the light source 5 and the sample chamber 4 and a second transparent region 7B is arranged between the sample chamber 4 and the photodetector 6. The transparent regions 7A and 7B may be of air or silicon oxide, silicon, polymers or other materials transparent to the wavelength of the light emitted by the source. As explained in detail hereinafter, the first transparent region 7A may embed an optical element 8 having the purpose of adjusting, for example widening, the light beam generated by the light source 5 and thus increasing the volume of particles within the detection area 4A that are simultaneously hit by the light beam.

The light source 5 may be implemented in any known way that enables its integration in the body 2. For instance, it is possible to use the optical radiation emitting device described in U.S. Pat. No. 6,661,035. Likewise, the photodetector may be implemented in various ways, for example as described in WO2014107504. The light source 5 may further include a plurality of emitting photodiodes 60 and the photodetector 6 may include a plurality of receiving photodiodes 61, as illustrated in FIG. 2.

The sample chamber 4 is closed at the top and at the bottom by first and second grids 10, 11, of conductive material, typically metal, such as aluminium, tungsten, gold, or copper.

Figure 3:
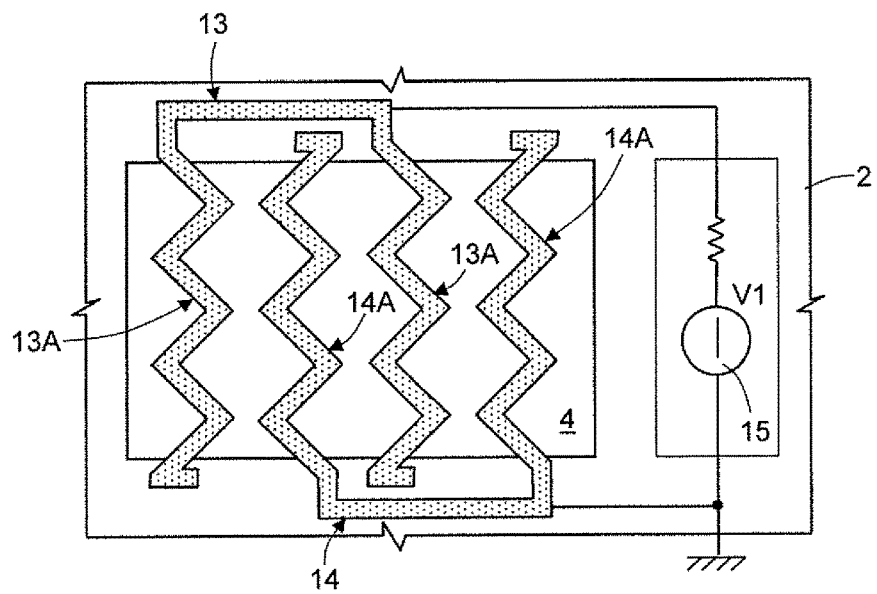
FIG. 3 is a schematic representation of a possible embodiment of a grid that may be used in the particle detector of FIG. 1.
Figure 4:
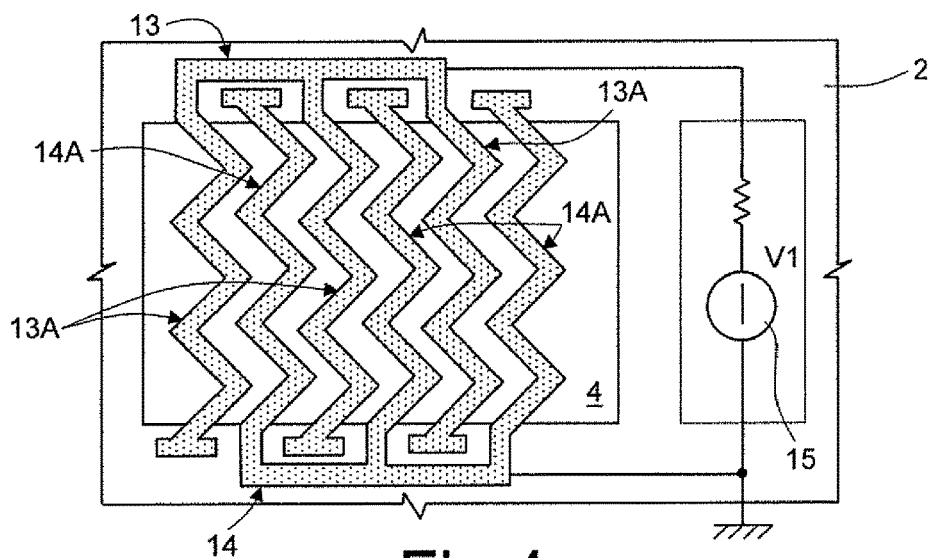
FIG. 4 is a schematic representation of another possible embodiment of a grid that may be used in the particle detector of FIG. 1.

In detail, the first grid 10 is formed on the second face 2B of the body 2 to form an ionizing grid having tips. In particular, with reference to FIGS. 3 and 4, the first grid 10 is formed by a pair of electrodes 13, 14. The electrodes 13, 14 are arranged in the same plane, extend parallel to the second face 2B of the body 2, and are comb-fingered. Furthermore, they are biased in opposite ways. For instance, in FIG. 3 each electrode 13, 14 comprises a plurality of zigzag-shaped branches 13A, 14A, and the tips of the branches of one electrode (for example, the tips of the branches 13A of the first electrode 13) are arranged facing the tips of the branches of the other electrode (for example, the tips of the branches 14A of the second electrode 14). In FIG. 4, instead, the branches 13A, 13B extend at a constant distance. The shapes shown have, however, merely an illustrative purpose, and many other configurations are possible, provided that they are able to ionize the passing gas, such as air.

Figure 5:
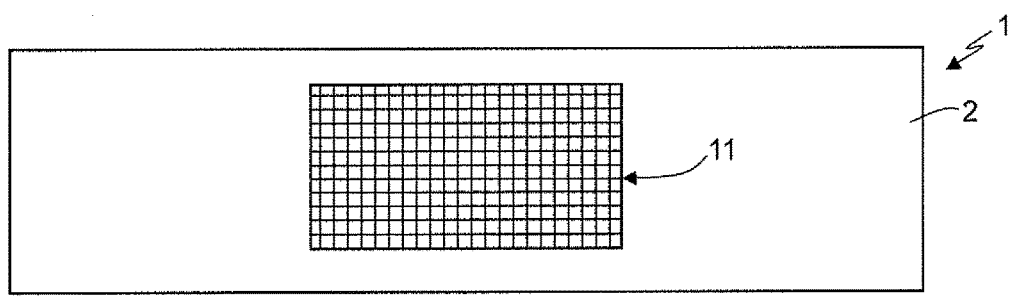
FIG. 5 is a schematic representation of a possible embodiment of another grid that may be used in the particle detector of FIG. 1.

The second grid 11, here formed on the first face 2A, is a simple conductive grid formed by a conductive metal layer having a plurality of holes of any shape, for example circular, square (as represented schematically in FIG. 5, forming a sort of grating), hexagonal or in general polygonal, arranged in an array, in a honeycomb configuration, or according to a regular or irregular pattern. The second grid 11 thus has only a function of attracting and accelerating the ionized molecules of gas, such as air, and the particles contained therein, and this function may be regulated and modified via an appropriate biasing potential applied on the second grid 11.

The substrate 20 may further integrate processing circuitry, as represented schematically in FIG. 1 and designated at 18. Alternatively, within the substrate 20 and on the faces 2A, 2B, regions for electrical connection to external processing units may be provided.

In use, a potential difference (represented by voltage generator 15 of FIGS. 3 and 4) is applied between the electrodes 13 and 14 of the first grid 10 and causes ionization of the gas, such as air, entering the sample chamber 4 through the first grid 10. Furthermore, the second grid 11 is biased at a voltage of opposite sign to the air ionization voltage. Application of high voltage, close to the air breakdown voltage, to the electrodes 13 and 14 causes liberation of electrons of the air molecules. The air molecules, thus positively charged, are attracted by the second grid, which is negatively biased, entraining with them any particles. In practice, the thus ionized air is attracted and accelerated within the sample chamber 4 through the detection area 4A by the second grid 11 and further undergoes compression, locally increasing its density, which may be increased also as a result of the shape of the concentration area 4B having a cross-section decreasing from the first grid 10 towards the detection area 4A. The number of particles to be detected that pass through the detection area 4A, entrained by the ionized air, is thus considerably increased in unit volume and/or unit time. In the detection area 4A, the accelerated and concentrated particles are hit by a light beam 12 emitted by the light generator 5 and cause scattering of the light. The thus scattered light is detected in a known manner by the detector 6, connected to a processing unit (not illustrated), for determining the number of particles and their size, which is correlated to the spatial distribution in the light-scattering area.

In practice, the ensemble of the grids 10, 11 and of the sample chamber 4 forms a gas pump 50 (FIG. 2), which accelerates and compresses the air forced through the sample chamber 4.

In this way, there is a considerable increase in the number of particles in the detection area 4A during measurement, thus increasing the detection efficiency of the particle detector 100.

In the first grid 10, the voltage to be applied between the electrodes 13 and 14 of the first grid 10 (the ionizing grid) is a function of the distance between the tips. This distance may be chosen as small as desired, with the limit of lithographic processes for defining metal layer. For instance, with current processes, electrodes may be easily produced with distances between the tips of less than 100 nm, even as little as 50 nm or less. For these distances between the electrodes 13 and 14, a d.c. voltage of 100 V or 50 V or less may be applied.

The biasing voltage of the second grid 11 in general depends upon the application and, in particular, the concentration of particles expected in the environment where the measurement is to be made. For measurements in environments with high concentration of particles to be measured, where the sample chamber 4 fills up fast with particles, it is possible to use lower voltages than in situations with low concentration. For instance, with voltages of 1-10 V it is possible to accelerate ionized air molecules for obtaining an increase of the concentration of the particles to be measured even by a factor of 10 or 100, filling the sample chamber 4 in just a few seconds. According to the geometries and to the sizes chosen, the second grid 11 may also be biased at higher voltages (for example, 100 V, 200 V), even without reaching the breakdown voltage of air.

In a possible implementation of the particle detector 100, the pitch of the second grid 11 may be such as to hold the particles of interest.

The data processing algorithm may then correlate the results of dimensional distribution and concentration of the particles to the effective concentration in the environmental gas, such as air, on the basis of known algorithms and by applying the basic laws of classical physics, carrying out a sort of "de-amplification" of the data read.

In a further possible embodiment, the first grid 10 may be a standard grid, similar to the second grid 11, and the voltage between the grids 10 and 11 ionizes and accelerates the air molecules. In a variant of this embodiment, the first grid 10 may also have a three-dimensional structure, with projections or tips directed vertically towards the inside of the sample chamber (and thus orthogonal to the second face 2B of the body 2). Furthermore, the projections or tips may face the second grid 11 for reducing the distance between the two grids 10, 11 and reduce the voltage applied thereto.

According to an embodiment of the particle detector 100, after the particles to be measured have been concentrated inside the sample chamber 4 and the measurement of the distribution of the particles has been carried out, it is possible to reverse the biasing of the grids 10, 11 and empty the sample chamber 4 through the first grid 10, thus also removing possible particles accumulated around the first grid 10.

The particle detector 100 may be manufactured as illustrated in FIGS. 6A-6F.

Figure 6A:
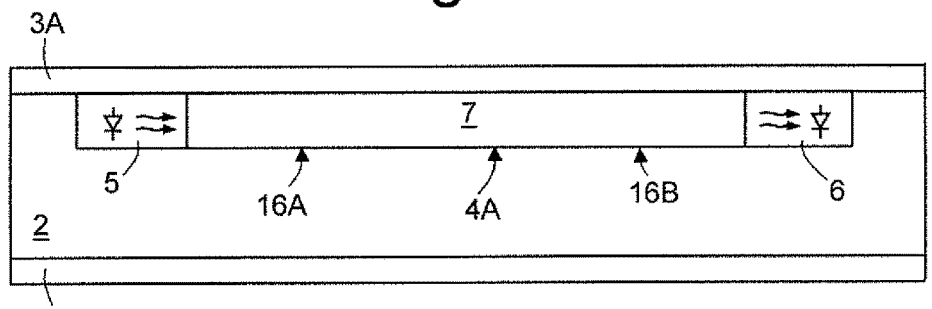
FIGS. 6A-6F are cross-sections similar to FIG. 1, in successive manufacturing steps.
Figure 6B:
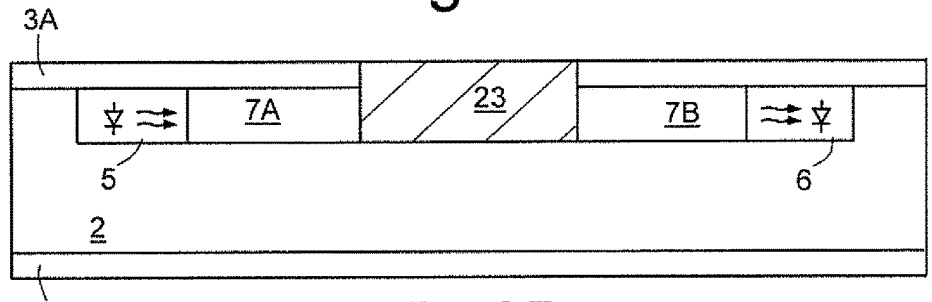

Initially and referring now to FIG. 6A, the optical source 5 and the photodetector 6 are integrated in the substrate 20, using microintegration techniques known in the semiconductor industry. In the same substrate, a cavity is formed, intended to define the detection area 4A (which is thus also referred to hereinafter as "detection cavity 4A"), and at least two optical cavities 16A and 16B are formed, to be filled by the material of the transparent regions 7A, 7B. In the cross-section of FIG. 6A, the detection and optical cavities 4A, 16A, 16B are aligned to one another, to the light source 5, and to the photodetector 6 and appear as a single cavity. Alternatively, and in presence of mirror structures, they may not be aligned, as discussed hereinafter. The cavities 4A, 16A and 16B are, for example, obtained by etching the silicon.

Next, the detection cavity 4A and optical cavities 16A, 16B are filled with the transparent material 7 that is to form the transparent regions 7A and 7B and, after a possible planarization, on top of and underneath the wafer 2 the protective layers 3A, 3B are formed, for example of dielectric material.

Next (FIG. 6B), the transparent material 7 is removed through a selective etch from the detection cavity 4A, and the latter is filled with a first sacrificial material 23, for example an oxide or a nitride.

Figure 6C:
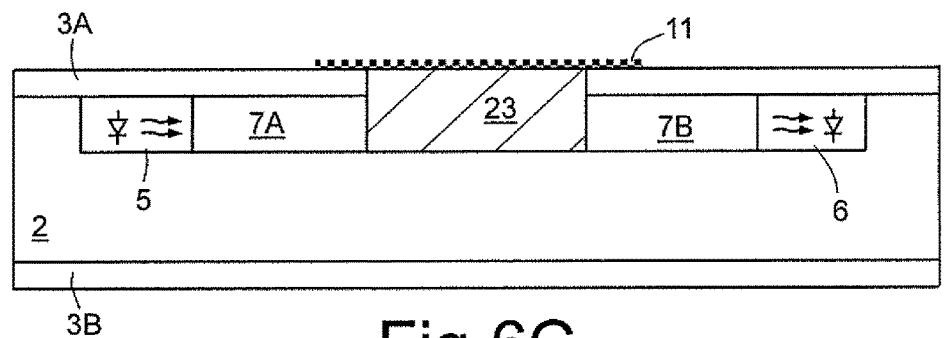
Figure 6D:
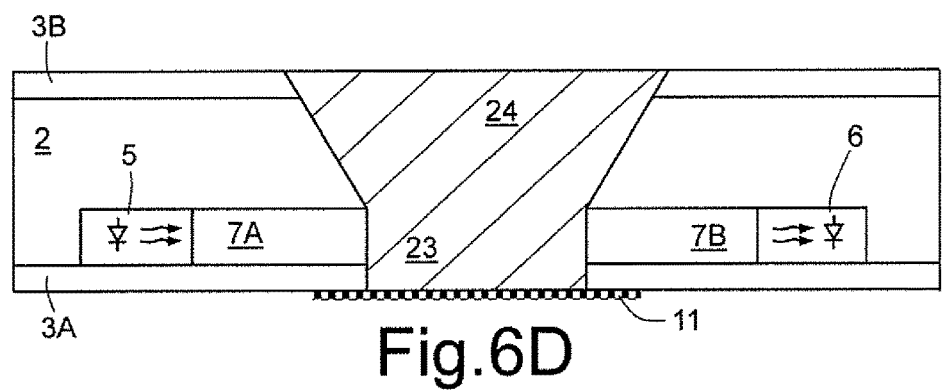

The second grid 11 is formed on top of the protective layer 3A (FIG. 6C). For this purpose, a metal layer is deposited and then defined, to obtain the desired shape.

Then (FIG. 6D), the substrate 20 is flipped over and etched for forming the concentration area 4B. For instance, a TMAH (tetramethyl ammonium hydroxide) etch or KOH (potassium hydroxide) etch may be used, which automatically stops at the first sacrificial material 23, to form the concentration area 4B. Then, the latter is filled with a second sacrificial material 24, for example an oxide or a nitride.

The first grid 10 is formed on the second face 2B of the wafer 2 (FIG. 6E), in a way similar to the second grid 11.

Figure 6E:
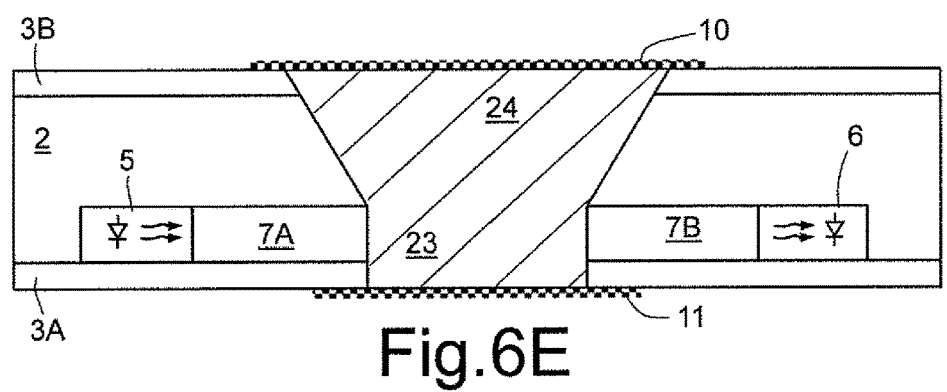
Figure 6F:
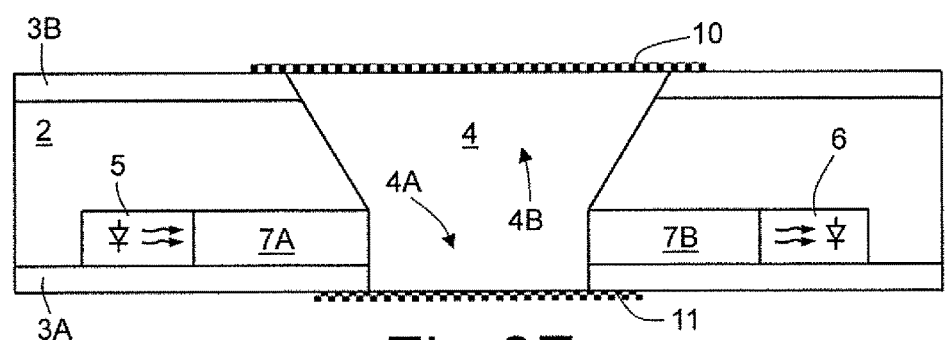

In a variant, before the step illustrated in FIG. 6E, i.e., before forming the first grid 10, through masking and etching, cavities may be formed in the second sacrificial material 24 so that, during the deposition of the material of the first grid 10, vertical tips are formed, thus creating a three-dimensional grid.

Next (FIG. 6F), the first and second sacrificial materials 23, 24 are removed through the first grid 10 and/or the second grid 11.

In a variant, the cavities 16A and 16B may be filled with gas, such as air. In this case, the material of the transparent regions 7A and 7B may be similar to the first and second sacrificial materials 23 and 24 and be removed together with the sacrificial materials.

Figure 7:
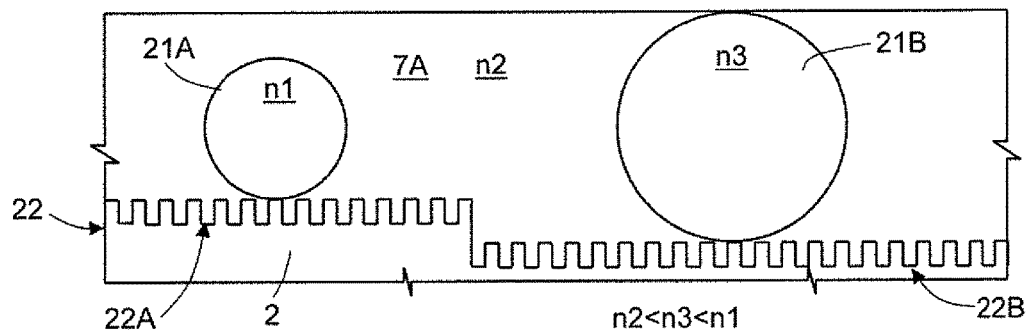
FIGS. 7 and 8 illustrate two possible embodiments of a detail of the particle detector of FIG. 1.
Figure 8:
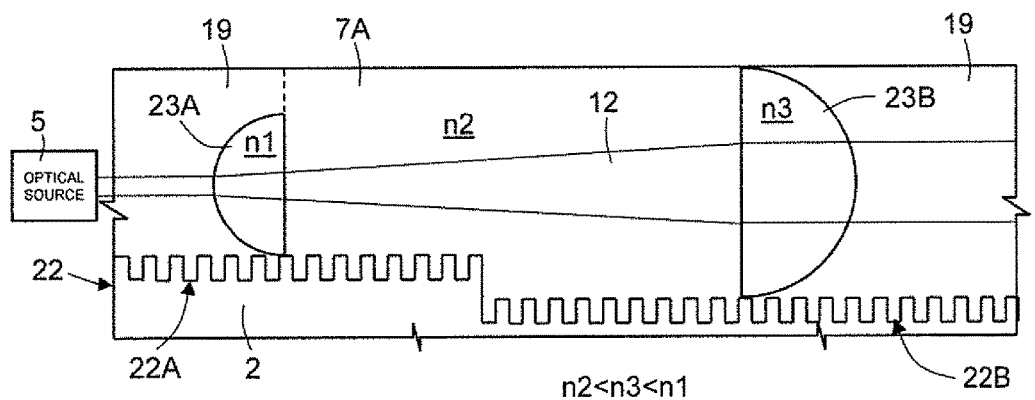

FIGS. 7 and 8 illustrate two possible embodiments of the optical adjustment element 8, for example for aligning and/or widening the light beam 12 generated by the light source 5.

In detail, in FIG. 7 the optical element 8 includes a pair of lenses 21A, 21B. The lenses 21A, 21B may be formed by balls of materials having suitable optical characteristics, for example resins or polymers or oxides with refractive index optimized through engineering of the structure or doping. Here, the hydrophobic surface 22 includes two portions 22A and 22B, having a different roughness and precisely the first portion 22A, bearing the first lens 21A, has a lower roughness than the second portion 22B, bearing the second lens 21B. Furthermore, the first lens 21A has a refractive index n1 greater than the refractive index n3 of the second lens 21B, which in turn has a refractive index greater than the refractive index n2 of the surrounding material (material of the first transparent region 7A or the second transparent region 7B or air), n2<n3<n1. The first lens 21A further has a smaller diameter than the second lens 21B and is arranged upstream of the second lens 21B, in the direction of the light beam 12 generated by the optical source 5.

For instance, the roughness of the hydrophobic surface 22 may be obtained by treating the silicon or other material deposited on silicon with suitable hydrophobic characteristics. The treatment may be carried out in a well-controlled way, for example through lithography and chemical etching (for example, silicon wet etching in $HNO_3+HF$). To obtain a spherical lens the surface may be superhydrophobic.

To obtain the lenses 21A, 21B, during manufacturing, drops of the optical material may be deposited on the surface 22, for example injected via a nozzle of an appropriate apparatus. As is known, the size of the drops depends not only on the surface tension of the deposited liquid, but also on the higher or lower hydrophobicity of the substrate obtained by varying the surface roughness. For instance, the period of the structures lines/spaces defined with known lithographic methods may be varied. Consequently, on the first portion 22A a drop of smaller size is formed, and on the second portion 22B a drop of larger size is formed. The drops thus deposited are hardened, for example via curing, for obtaining the lenses 21A, 21B. Next, the transparent material that is to form the transparent regions 7A, 7B, if any, is deposited. It should be noted that, even though during hardening the size of the lenses 21 may undergo a reduction, the system may be designed to take into account this reduction in order to obtain lenses 21 of the desired size.

The above manufacturing mode may be advantageously used also for forming one or more lenses of an optical system for alternative applications, for example in photonics, where for example an alignment of the light beam is useful.

FIG. 8 illustrates, instead, an optical element 8 including two lenses 23A, 23B of a convergent type, so that the light beam 12 exiting the optical element 8 is parallel. This solution is obtained after forming the lenses 21A and 21B as described with reference to FIG. 7. In this case, after curing the drops, a sacrificial material 19 is deposited, for example the same material as the transparent regions 7A, 7B, and is lithographically defined, and the lenses 21A and 21B are etched (for example, via dry etching in $O_2$ plasma and a fluorinated gas, such as $CF_4$ or SF or $NF_3$) for removing the respective mutually facing portions thereof. Next, the space previously occupied by the sacrificial material 19 is possibly filled with the material of the transparent regions 7A, 7B, after any additional processes for removing the sacrificial material 19.

According to another embodiment, the optical system 8 may be more complex and include spherical lenses as in FIG. 7 (the lens 21A and/or the lens 21B) formed with a different process (for example, premolded and then introduced into the particle detector). In other applications, such as for example in photonics, the lenses may be used also individually, for example, for the same purposes.

Another method for forming the lenses 21, 23 is based upon the hydrophobicity-modifying capacity of a material by applying suitable potentials to the substrate. This technique also referred to as "electrowetting" is described, for example, in "Dielectric materials for electrowetting-on-dielectric actuation", Hong Liu, Saman Dharmatilleke, Devendra K. Maurya, Andrew A. O. Tay, Microsyst. Technol. (2010) 16:449-460.

Figure 9:
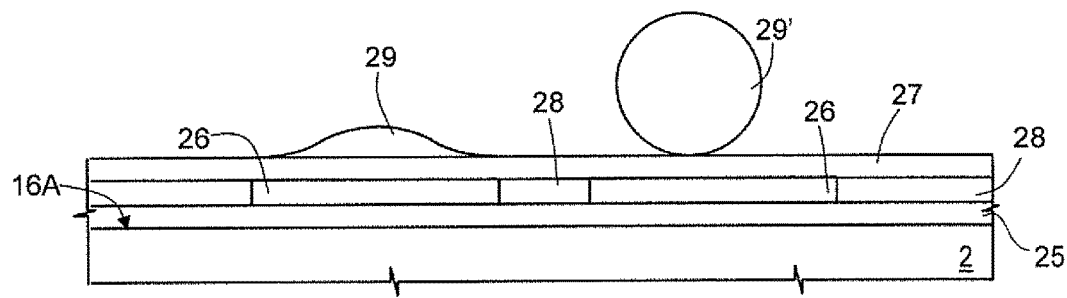
FIG. 9 illustrates a manufacturing sequence of the detail of FIGS. 7 and 8.

In this case, as illustrated in FIG. 9, the bottom of the area of the body 2 where the optical element 8 is to be provided (bottom of the first cavity 16A) has an insulating layer 25, for example silicon oxide, a dielectric layer 28 that separates electrode regions 26, for example metal regions, and a variable-hydrophobicity layer 27, of an insulating type, for example of an oxide, a polymeric material or a resin, such as polyimide or parylene or Teflon®. In particular, the variable-hydrophobicity layer 27 is of a material the hydrophobicity whereof may be electrically modified by applying appropriate voltages.

During manufacture of the particle detector 100, before depositing the material of the first transparent region 7A, using standard techniques in the semiconductor industry, the insulating layer 25, the electrode regions 26, the dielectric layer 28, and the variable-hydrophobicity layer 27 are first formed. Then, on the electrode regions 26, some drops 29 of transparent material are deposited, for example a resin or a polymer, in liquid phase and not yet shaped (as illustrated in the left-hand part of FIG. 9). Next, through the electrode regions 26, a suitable potential, depending on the material of the variable-hydrophobicity layer 27, for example a voltage of 25 V or 120 V (see also Tables 1 and 2 of the article cited above) is applied to the drops 29.

To this end, a further electrode (not illustrated) may be applied on the drops 29 and be capacitively coupled to the electrode 26, in contact or not with the drops 29. This electrode may form part of appropriate equipment designed to form the lenses via electrowetting to get the optical material of the drops 29 to harden, exploiting, for example, a thermal chuck carrying the wafer 2 of semiconductor material.

The applied voltage causes an increase of the hydrophobicity of the variable-hydrophobicity layer 27 and, consequently, modification of the wettability and shape of the drops 29, which assumes a generally spherical shape, as shown and designated at 29' in the right-hand part of FIG. 9.

The above effect may also be enhanced by treating the surface of the hydrophobic layer 27 to render it rough, as described with reference to FIGS. 7 and 8. Next, part of the lens 29 may be removed, as in FIG. 8.

Figure 10:
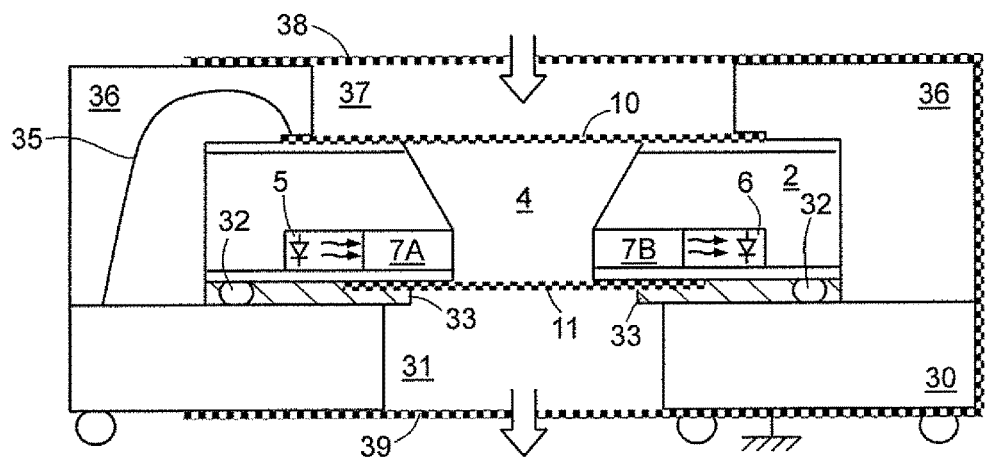
FIG. 10 illustrates a possible package of the particle detector of FIG. 1.

The particle detector 100 may be packaged as illustrated in the example of FIG. 10. Here, the body 2 is bonded to a support 30 having a through hole 31 aligned to the cavity of the sample chamber 4. Bumps 32 may be provided for fixing and electrically connect the body 2 to the support 30. A perforated insulating layer 33 may be arranged between the support 30 and the body 2. A package 36 surrounds the body 2 at the sides and at the top and embeds the electric connection wires 35. The package 36 also has an opening 37 on top of the sample chamber 4 to enable passage of gas, such as air, through the body 2.

A third grid 38 may be provided on top of the opening 37 and, on the opposite side, a fourth grid 39 may be provided underneath the through hole 31.

The third and fourth grids 38, 39, which are also, for example, obtained by patterning a deposited metal layer and/or by bonding respective preformed grids that may be provided as a single grid extending over three sides of the package 36, may have a safety function to prevent accidental contact with objects or persons during handling. Further, they may prevent foreign material having a larger size than the holes of the grids 38, 39 from penetrating into the sample chamber 4.

Figure 11:
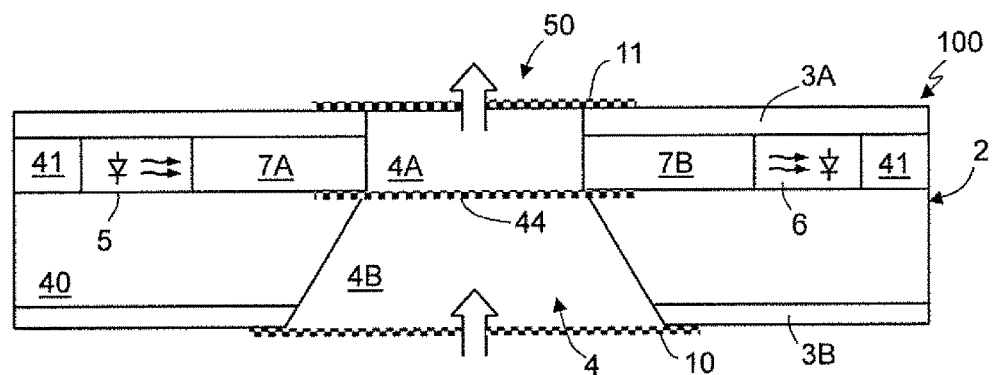
FIGS. 11-13 illustrate different embodiments of a particle detector.

FIG. 11 illustrates a different embodiment of the particle detector 100. Here, the body 2 is formed starting from two substrates 40, 41 bonded together, where a first substrate 40 carries the first grid 10 and a second substrate 41 carries the second grid 11. Furthermore, the second substrate 41 accommodates the light source 5, the detection area 4A, the photodetector 6, and the transparent regions 7A, 7B, while the first substrate 40 accommodates the concentration chamber 4B. Here, a control grid 44 is formed between the first and second substrates 40, 41. The protective grid 44 may be electrically insulated from the first substrate 40 and/or the second substrate 40, 41 via an insulating layer (not illustrated), such as for example an oxide.

The protective grid 44 may be biased at an intermediate voltage in order to increase the efficiency of the gas pump 50 and/or control the concentration of the particles in the detection area 4A.

According to an alternative (not illustrated), the first protective layer 3A of FIGS. 1, 10, 11 is replaced by a third semiconductor substrate, and the second grid (acceleration grid 11) may be provided, for example, between the substrate 20 (second substrate 41) and the third wafer.

Figure 12:
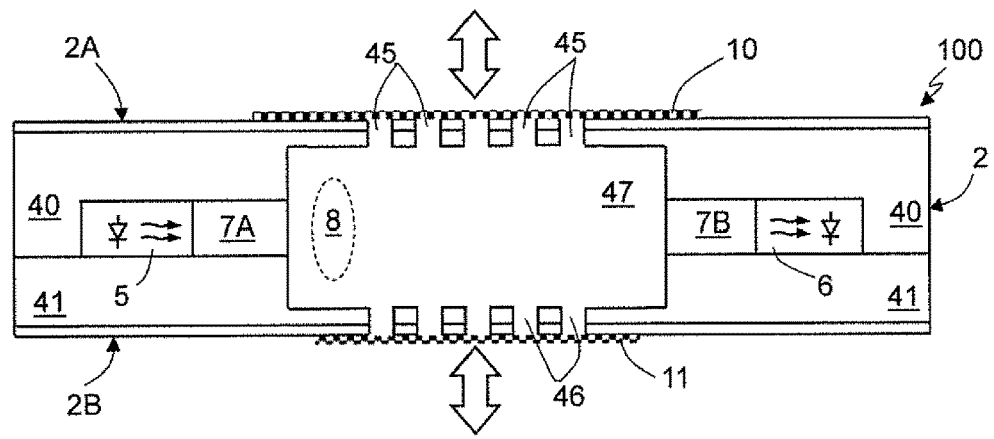

FIG. 12 illustrates an embodiment where, as compared to FIG. 11, a detection area 47 extends at a distance from the first and second faces 2A, 2B of the body 2 and is connected to the outside through a first plurality of holes 45 in the first substrate 40 and through a second plurality of holes 46 in the second substrate 41. In this case, the first and second grids 10, 11 may be arranged on the first and second faces 2A, 2B, respectively (as illustrated), or inside the body 2 on the bottom of the detection chamber 47, respectively between the detection chamber 47 and the holes 45, on one side, and between the detection chamber 47 and the holes 46, on the other side, before coupling of the two substrates 40, 41.

Figure 13:
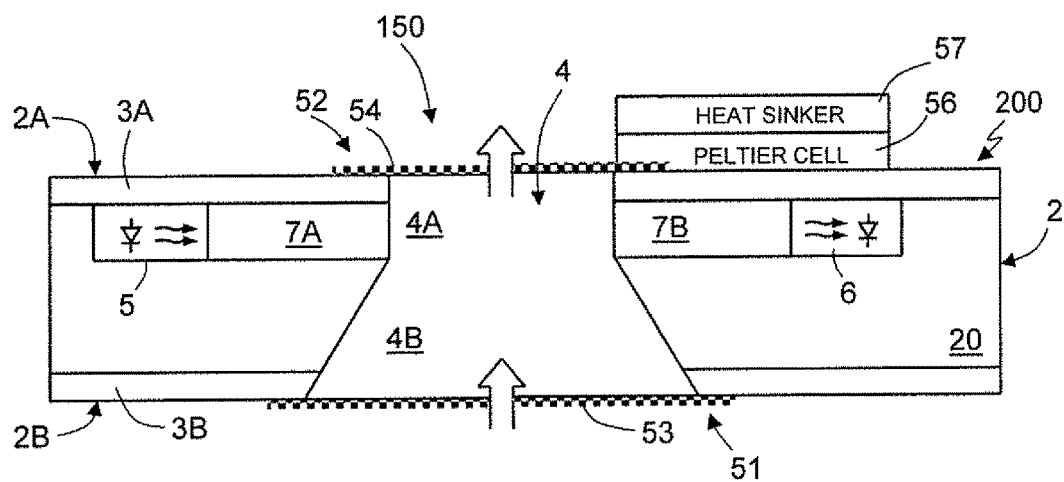

FIG. 13 illustrates a particle detector 200 having a gas pump 150 operating in a thermal way. To this end, a heating structure 51 is formed at one end of the sample chamber 4, and a cooling element 52 is formed at another end of the sample chamber 4. For instance, in FIG. 13 the body 2 is provided as shown in FIG. 1, and includes the first substrate 20 integrating the light source 5 and the photodetector 6 and accommodating the sample chamber 4. The heating structure 51 is formed on the end of the concentration area 4B of the sample chamber 4, and includes a heating grid 53 formed by a simple conductive grid configured so as to allow current flow and heat generation by the Joule effect. Alternatively, the heating grid 53 may be thermally in contact with a heating element (not illustrated), such as for example a resistor. The cooling element 52 is formed by a cooling grid 54 and by a thermoelectric device 56, such as a Peltier cell, in mutual thermal contact. The cooling element 52 may further include a heat dissipator or sinker 57 in thermal contact with the Peltier cell 56.

In use, the heating structure 51 is fed with current and is heated by the Joule effect. Simultaneously and in a known way, the Peltier cell 56 that cools the cooling grid 54 is supplied. The temperature difference existing between the heating structure 51 and the cooling element 52 thus causes movement of gas, such as air, from the heating structure 51 towards the detection area 4B and the cooling element 52 and, thus, intake of other air from outside through the heating structure 51. The temperature difference thus creates a "pump" effect, which accelerates the air and the particles contained therein, concentrates them and forces them into the detection chamber 4A, as described above for the ionic pump 50 with reference to FIG. 1. Also here, the grid 52 may have a pitch such as to hold the particles of interest.

Figure 14:
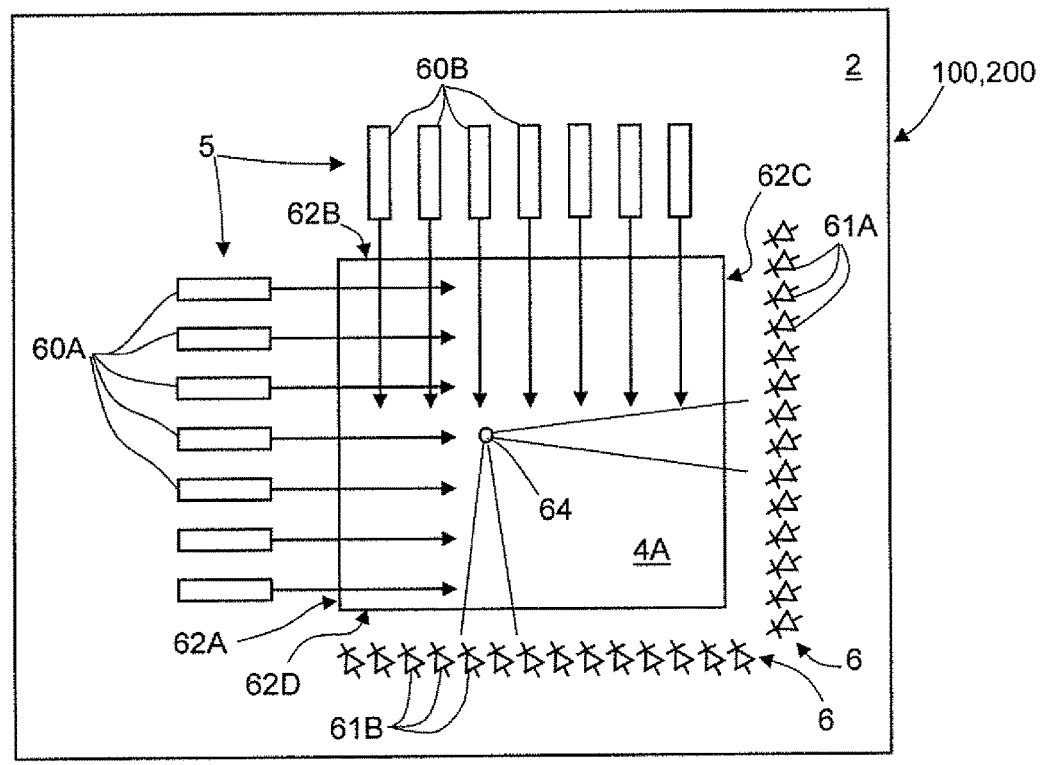
FIG. 14 is a schematic top plan view of a different embodiment of another detail of the particle detector of FIGS. 1-13.

FIG. 14 illustrates an embodiment of the optical system 8, which may be used both for the particle detector 100 of FIGS. 1-12 and for the particle detector 200 of FIG. 13, and has the aim of increasing the accuracy and efficiency of detection. Here, the light source 5 comprises two pluralities of light-emitting elements 60A, 60B, arranged on two adjacent sides 62A, 62B of the detection area 4A, having a generally square area in top plan view. Furthermore, the photodetector 6 includes two corresponding pluralities of receiving photodiodes 61A, 61B, for example with PN junction, arranged on two sides 62C, 62D of the detection area 4A opposed to the sides 62A, 62B of the light-emitting elements 60. For instance, the receiving photodiodes 61 may have a structure of a P-I-N type, as illustrated in U.S. Pat. No. 4,210,923. Furthermore, at least one of the light sources may emit more than one wavelength.

According to another variant (not illustrated), the particle detector 100, 200 may include only a plurality of light-emitting elements 60A and a corresponding plurality of receiving photodiodes 61A. The presence of one or more pluralities of light-emitting elements 60A (or 60B) contributes to widening the light beam. This approach may thus replace the optical element 8 of FIG. 1.

Again according to another variant, only the light-emitting elements 60A (or even only one of them) and the receiving photodiodes 61B may be provided. In this way, only the light scattered around the orthogonal direction is detected.

In a way not illustrated, optical elements 8 may be provided between the light-emitting elements 60 and the detection area 4A, as in FIG. 1, for enabling multiple measurements also in a vertical direction (perpendicular to the drawing plane).

With the approach of FIG. 14, it is possible to simultaneously make multiple measurements since a particle 64 may be struck by a number of light beams and give rise to a number of scattered light beams that may be detected by more than one receiving photodiode 61A, 61B on both sides 62C, 62D of the detection area 4A.

Likewise, in a way not illustrated, it is possible to arrange a plurality of light-emitting elements 60, 60A, 60B and/or a plurality of receiving photodiodes 61, 61A, 61B stacked vertically, i.e., in the direction of the thickness of the body 2, perpendicular to its faces 2A, 2B, for example by stacking a number of dice integrating the elements.

Figure 15:
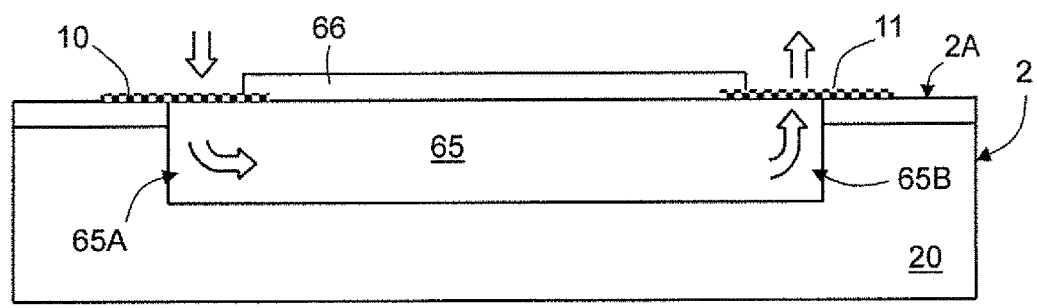
FIGS. 15 and 16 illustrate a cross-section and a top plan view, respectively, of an embodiment of a particle detector with a different conformation of the sample chamber.
Figure 16:
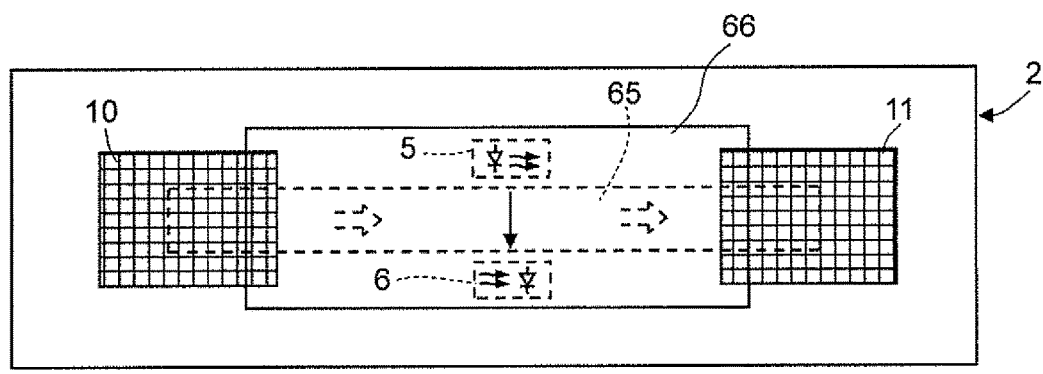

FIGS. 15 and 16 illustrate a different conformation of the sample chamber of the particle detector 100, 200. Here, the sample chamber 65 is not a through cavity, but extends parallel to the faces 2A, 2B of the body 2. In the example illustrated, an elongated cavity extends into the substrate 20, facing, for example, the first face 2A and having a first end 65A and a second end 65B. The first and second grids 10, 11 are both formed on the first face 2A, on the first end 65A and the second end 65B, respectively. A closing layer 66 extends over the sample chamber 65. The closing layer 66 may be of any suitable material, transparent or not, for example an oxide or a polymeric material or may be formed by a die.

The light source 5 and the photodetector 6 may be arranged on any two opposed sides of the sample chamber 65, for example on two opposed longitudinal sides, as illustrated schematically in FIG. 16.

Figure 17:
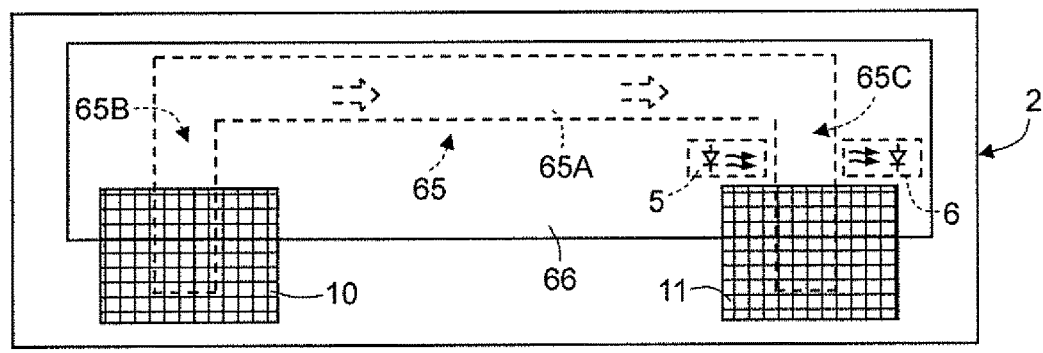
FIG. 17 is a top plan view of a different conformation of the sample chamber.

According to another embodiment illustrated in FIG. 17, the sample chamber 65 may be C-shaped in top plan view, having a longitudinal stretch 65A and two and two input and output stretches 65B, 65C, substantially coplanar to the longitudinal stretch 65A, so that the alignment axis of the grids 10, 11 does not coincide with the axis of the longitudinal stretch 65A. In this case, the light source 5 and the photodetector 6 may be arranged at the sides of the longitudinal stretch 65A or of the inlet stretch 65B or, as illustrated, of the outlet stretch 65C.

Other forms are obviously possible. For example, the cavity forming the sample chamber 65 may be formed by a buried cavity and extend at a distance from a major surface of the substrate 20, as described hereinafter with reference to FIG. 18.

Figure 18:
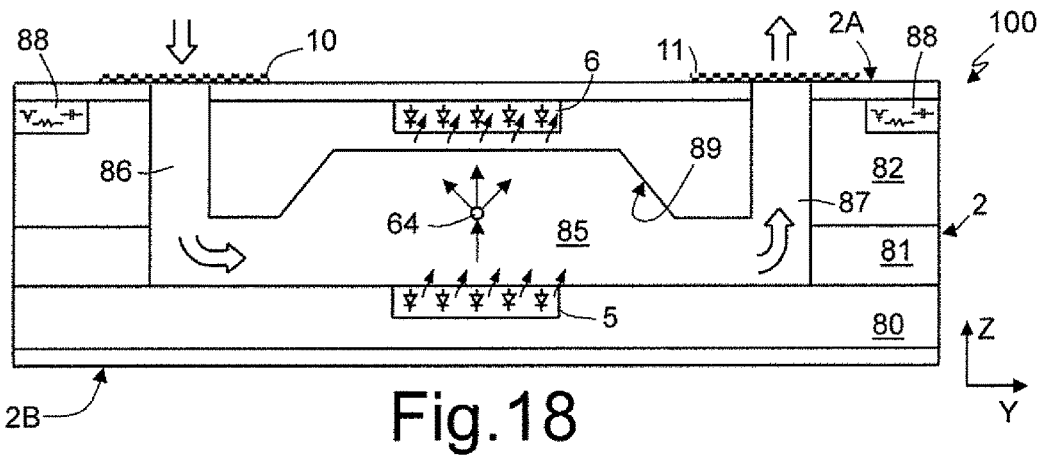
FIG. 18 is a cross-section of an embodiment of a particle detector.

FIG. 18 illustrates a solution where the detection area extends longitudinally and parallel to the faces 2A, 2B of the body, as illustrated in FIGS. 15-17, but the optical system 5, 6 is arranged perpendicular to the faces 2A, 2B of the body 2.

Here, the body 2 comprises three substrates 80-82 bonded together. In particular, a first substrate 80, adjacent to the second face 2B of the body 2, accommodates the light source 5. A second substrate 81 is in an intermediate position and surrounds part of the detection area 85, here having an elongated shape and oriented generally parallel to the faces 2A, 2B of the body 2, like the detection area 65 of FIGS. 15 and 16. A third substrate 82, adjacent to the first face 2A of the body 2, forms air inlet and air outlet channels 86, 87, which extend transversely to and between the detection area 85 and the first face 2A for connecting the detection area 85 to the outside.

The second substrate 81 enables an increase of the height of the detection area 85, but may be eliminated according to the height chosen for the detection area 85.

The first and second grids 10, 11 are both formed on the first face 2A of the body 2, at the air inlet and air outlet channels 86, 87, respectively.

The light source 5 is integrated in proximity of the surface of the first substrate 80 facing the detection area 85. The third substrate 82 further accommodates the photodetector 6, in a position facing the light source 5, and processing electronics 88. In the illustrated example, the photodetector 6 is integrated in proximity of the first face 2A of the body 2 and, to reduce the distance between the photodetector 6 and the detection area 85 as well as to increase the dimensions of the detection area 85, the third substrate 82 has a cavity 89 facing the second substrate 81 so that the detection area 85 also extends into the third substrate 82. Alternatively, the cavity 89 may be absent and the photodetector 6 may be integrated in proximity of the buried face of the third substrate 82, facing the second substrate 81, before bonding the substrates 81-82, and be connected to the processing electronics 88 via through connections, in a per se known manner, not illustrated.

According to a variant, the particle detector 100 of FIG. 18 may be formed in just two substrates arranged on top of one another. For instance, the second substrate 81 may be missing, and the detection area 85 may be provided as a cavity in the third substrate 82 that directly faces the first substrate 80 and is connected to the outside world through the air inlet and air outlet channels 86, 87.

The vertical implementation of the optical system of FIG. 18, with two or three substrates, has the advantage that it is possible to provide the light source 5 and the photodetector 6 in two different substrates 80 and 82, which are then optimized separately using different materials that are not always easily and completely compatible. In fact, for forming the light source 5 and the photodetector 6 having the same wavelengths, currently different active materials are used that are not compatible. For example, in the case of infrared light, GaAs or InP may be used to form the light source 5, but these materials are incompatible for example with Ge, which may currently be used for detecting infrared light.

In FIG. 18, both the light source 5 and the photodetector 6 may be formed by two-dimensional arrays of elements 60, 61.

In a variant (not illustrated), it is possible to form two or more gas pumps series connected on the fluidic path defined by the air inlet and air outlet channels 86, 87 and by the detection area 85, providing other grids similar to the grids 10, 11 at an intermediate position.

In an embodiment, the light source 5 may generate polarized light. In this case, the photodetector 6 may include an element for separating the polarized components of the light.

Figure 19:
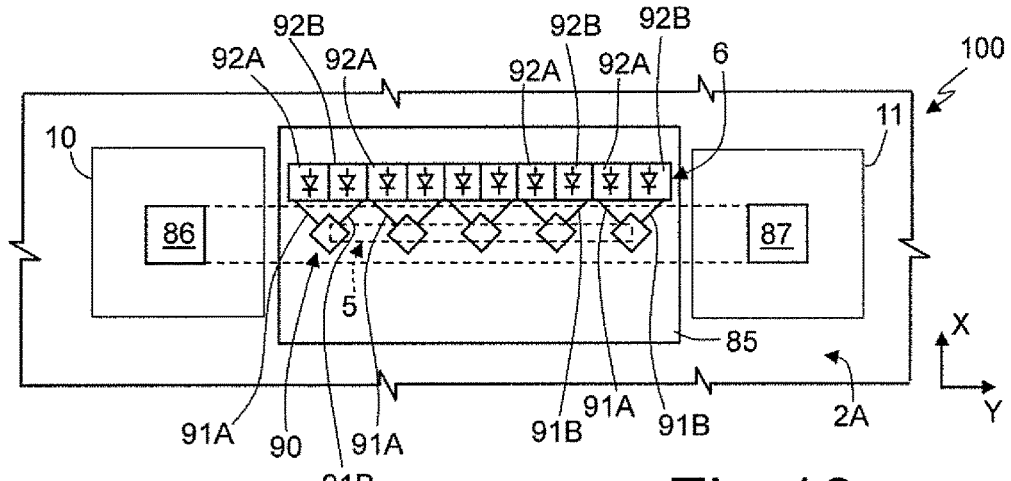
FIG. 19 is a top plan view of a different configuration of the photodetector of FIG. 18.

For instance, in FIG. 19 the particle detector 100, which has the general structure illustrated in FIG. 18, comprises a photodetector 6 including a light splitter 90 and a plurality of photodiodes 92A and 92B. The light splitter 90 may be formed, for example, by a polarization splitting grating coupler, such as the one described in "A Grating-Coupler-Enabled CMOS Photonics Platform" by Attila Mekis et al., IEEE Journal of Selected Topics in Quantum Electronics, Vol. 17, N. 3, May/June 2011, arranged on top of the light source 5.

For instance, the light source 5 may generate polarized light. Consequently, the two orthogonal polarized components of the light scattered by the particles in the detection area 85 hit at an appropriate angle upon the surface of the lattice 90 and are separated here. The incidence angle of the light on the surface of the lattice is optimized, for example by misaligning the photodetector 6 with respect to the light source 5 in the respective planes XY, or with a surface etching process that enables inclination thereof.

In particular, the light splitter 90 comprises two orthogonal structures of periodic lines cut in the material with lithographic and etching processes typical of the semiconductor industry. The lines of the two structures are oriented at ±45° with respect to an X axis belonging to the plane XY of the first face 2A of the body 2. The two orthogonal structures efficiently transmit the light with a polarization parallel to the lines, then separate the two components of the incident light with orthogonal polarization, and generate two light beams 91A, 91B with single polarization emitted at ±45° with respect to the X axis, which propagate in a respective optical waveguide (not illustrated). The photodiodes 92A, 92B are arranged so that each may receive a respective beam 91A, 91B.

The solution of FIG. 19 enables an improvement in the measure accuracy since the light polarization enables more precise calculation of the size of the particles to be detected on the basis of the distribution intensity of spatially scattered light.

The same solution may be applied also to the particle detector illustrated in FIGS. 1-17, with horizontal optical system, by adding appropriate mirrors.

Figure 20:
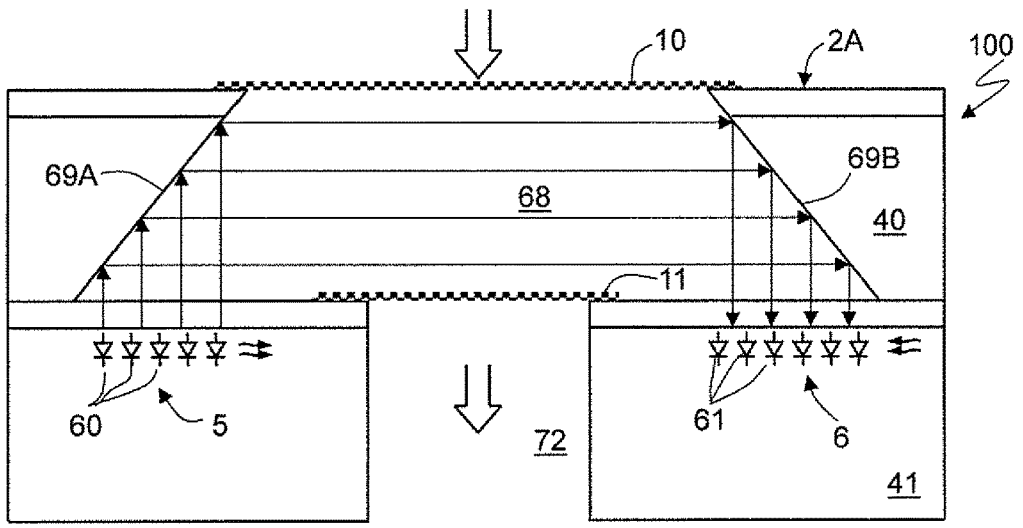
FIGS. 20 and 21 are cross-sections of different embodiments of a particle detector.

FIG. 20 illustrates an embodiment where the light source 5 and the photodetector 6 are not aligned and in view, and the detection area 68 has reflecting inclined walls for deflecting the light beam generated by the light source 5.

In detail, in the embodiment illustrated in FIG. 20, the particle detector 100 is formed in a body 2 having two substrates 40, 41 bonded together. Here, the detection area 68 is formed in the first substrate 40 and has a generally frusto-pyramidal shape, the minor base whereof is coplanar to the first face 2A of the body 2 and is closed by the first grid 10 and the major base whereof is substantially coplanar to the second grid. The detection area 68 thus has a height equal to the thickness of the first substrate 40. At least two opposed oblique sides of the detection area 68 are coated with a respective reflecting layer 69A, 69B, for example of gold or aluminium, each forming a mirror.

In FIG. 20, the light source 5 is formed in the second substrate 41, fixed to the first substrate 40 on the side forming the major base of the frusto-pyramidal detection area 68. A through hole 72 extends throughout the thickness of the second substrate 41 and ends at the second grid 11. The light source 5 is formed on one side of the through hole 72, here, for example, having a cylindrical, cubic, or parallelepipedal shape, and the photodetector 6 is formed on the other side. The light source 5 and the photodetector 6 are arranged facing the oblique walls of the detection area 68 so that the laser light emitted by the light source 5 hits the side wall (mirror 69A) facing it, is reflected towards the inside of the detection area 68, where it may be hit by particles entrained by the air ionized by the first grid 10 and be scattered by them. The scattered light may then be reflected by the second oblique wall (mirror 69B) towards the photodetector 6 facing it.

Also in this case, the light source 5 and the photodetector 6 may be formed by a plurality of emitting elements 60 and, respectively, receiving elements 61. Furthermore they may be each arranged on two adjacent sides of the through hole 72, as illustrated in FIG. 14.

Figure 21:
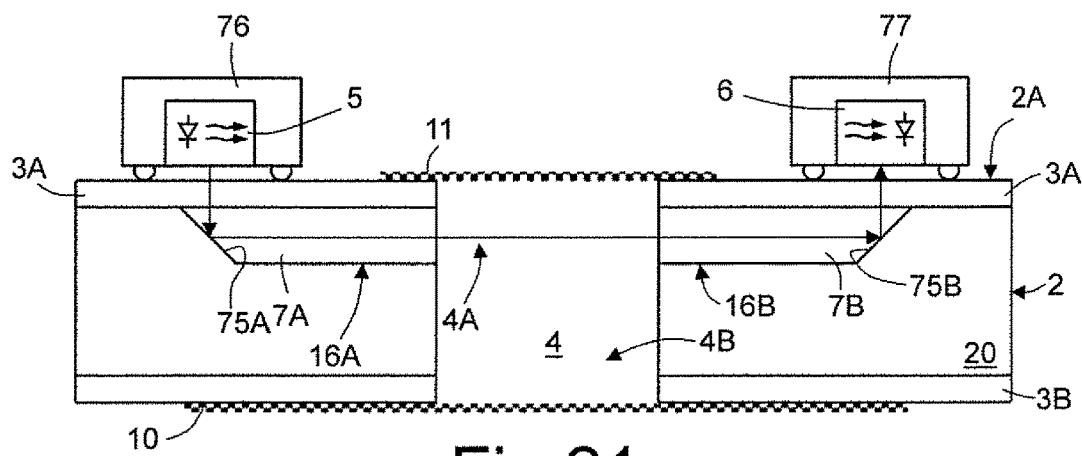

FIG. 21 illustrates a discrete solution, where the light source 5 and the photodetector 6 are formed in separate integrated devices fixed to the body 2 accommodating the sample chamber.

In detail, in FIG. 21 the sample chamber 4 is formed as in FIG. 1 and thus comprises a detection area 4A and a concentration area 4B, and the grids 10 and 11 are formed on the face 2A (adjacent to the detection area 4A) and on the face 2B (adjacent to the concentration area 4B) of the body 2, respectively. Also here, on two opposite sides of the detection area two cavities 16A, 16B accommodate the transparent regions 7A and 7B. Here, the bottom walls of the cavities 16A, 16B, remote from the detection area 4A, are oblique and are coated with respective reflecting layers (mirrors 75A, 75B). In particular, the bottom walls and the mirrors 75A, 75B are inclined in a direction such that the cavities 16A and 16B have, in the cross-section of FIG. 21, the shapes of isosceles trapezia, with the major bases facing the face 2A of the body 2.

In FIG. 21, the first protective layer 3A is of transparent material, for example polysilicon, silicon oxide, or a polymer, or has windows of transparent material in the entry and exit points of the light beam.

A first and a second integrated device 76, 77, which integrate the light source 5 and the photodetector 6, respectively, are fixed to the face 2A of the body 2 and face the mirrors 75A, 75B. In this way, as for the solution of FIG. 20, the light emitted by the light source 5 is reflected on the mirror 75A before reaching the detection area 4A, and the light scattered by the particles is reflected on the mirror 75B before being detected by the photodetector 6.

Figure 22:
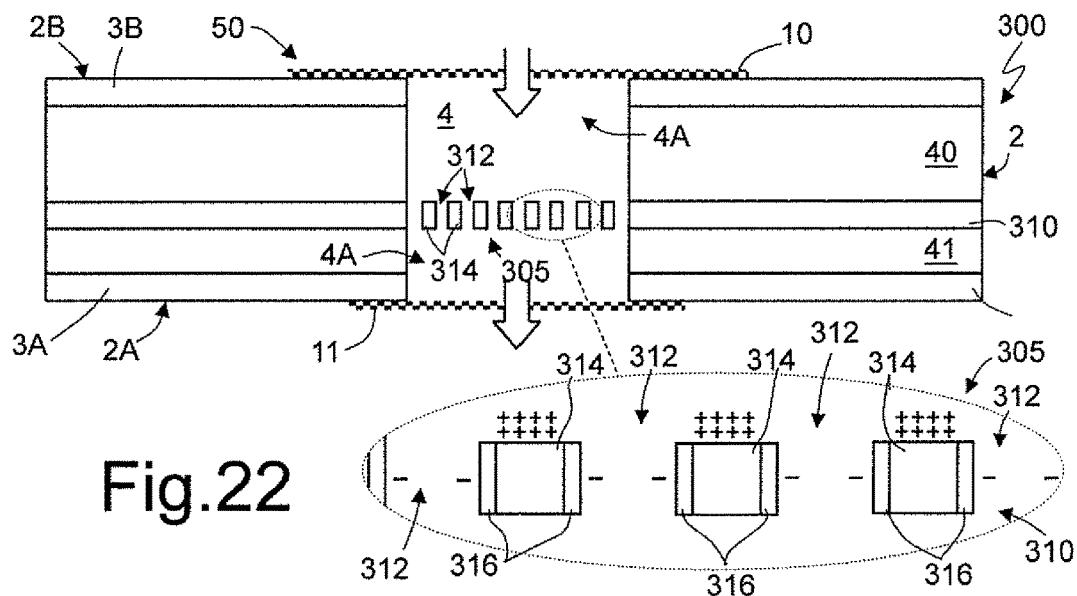
FIGS. 22 and 23 are cross-sections of embodiments of a device for detecting gases, such as radon.
Figure 23:
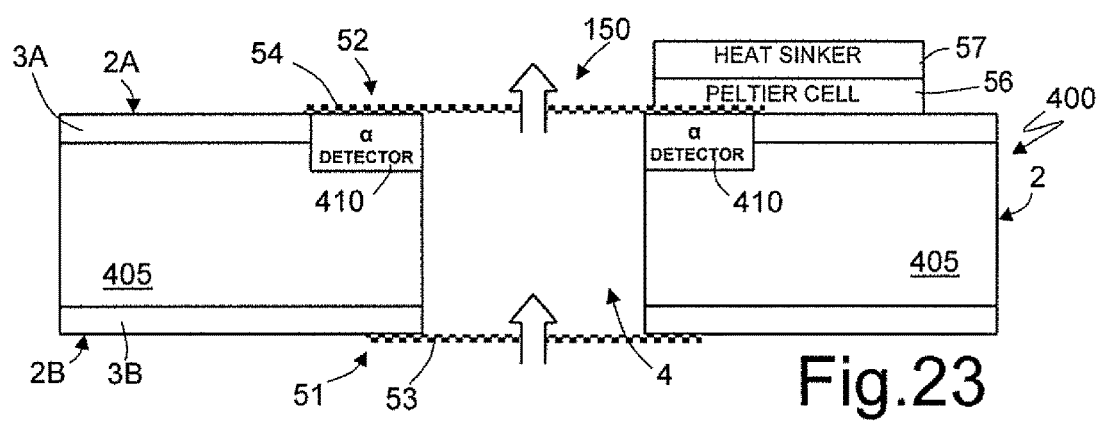

FIGS. 22 and 23 illustrate detectors for gas, such as radon, based upon detection of alpha particles.

In detail, FIG. 22 illustrates a gas detector 300 arranged in the body 2 and having a general structure similar to that of the particle detector 100 of FIG. 11, with the ionic gas pump 50. In particular, the body 2 is formed by two substrates 40, 41, which accommodate the sample chamber 4. The sample chamber 4 is also here divided into two areas 4A and 4B, formed in the first substrate 40 and in the second substrate 41, respectively, and is delimited on one side (the second face 2B) by the first grid 10 for air ionization and on the other side (the first face 2A) by the second grid 11, having an attraction function.

In FIG. 22, an alpha particles detecting structure 305 is formed in a third substrate 310 extending between the first and second substrates 40, 41. In detail, the alpha particles detecting structure 305 extends within the sample chamber 4 between the two areas 4B and 4A.

The portion of the third substrate 310 extending in the sample chamber 4 and forming the alpha particles detecting structure 305 has a plurality of through holes 312 for the passage of air and in the portions between the through holes 312 forms an array of sensitive areas 314. The walls of the sensitive areas 314 are coated with conductive material forming electrodes 316. The sensitive areas 314 may be formed in any known way, for example as described in U.S. Pat. No. 7,847,360, filed in the name of the present applicant.

As has been mentioned, the gas detector 300 has a gas pump 50 of an ionic type, and thus shaped and operating in a way similar to what described with reference to particle detector 100.

In use, the grid 11, and possibly the electrodes 316, are biased at an appropriate voltage (e.g., 100 V) for attracting the air molecules, which are positively biased by the ionizing grid 10 of the ionic pump 50, and the decay products. The sensitive regions 314 may thus detect the alpha particles emitted in proximity of the sensitive areas 314 by radon, by its decay-daughter products or by other radioactive elements contained in the air, accelerated by entrainment by the ionized air molecules.

FIG. 23 illustrates a gas detector 400 having a gas pump 150 operating in a thermal way, as described with reference to FIG. 13.

In particular, the body 2 is formed by a substrate 405 accommodating the sample chamber 4. A heating grid 53 is formed at a first end of the sample chamber 4, on the second face 2B of the body 2, and the cooling element 52 (also here a grid 54 arranged thermally in contact with a Peltier cell 56) is formed at a second end of the sample chamber 4, on the first face 2A of the body 2.

A detector of alpha particles 410 is arranged at the sides of the sample chamber 4, in proximity of the cooling grid 54, functionally similar to the sensor described in U.S. Pat. No. 7,847,360, but modified in order to take into account the direction of the alpha particles, i.e., horizontal instead of vertical. For instance, the alpha-particle detector 410 is integrated in the substrate 405 and faces the side wall of the sample chamber 4. Alternatively, the detector may be separately processed in a silicon wafer and then positioned with packaging processes (System in package) of the flip-chip type, with the silicon arranged vertically.

The sample chamber 4 may have any shape in a cross section of the drawing plane of FIG. 23. For instance, the sample chamber 4 may have an elongated rectangular cross-section, with one much greater dimension than the other. In this way, a high detection efficiency is achieved.

The alpha particles emitted by the radon flowing with the environmental air through the sample chamber 4, as a result of the heat pump 150, may thus be detected in shorter times by the alpha-particle detector 410, maintaining the correlation with the concentration in the natural environment.

The gas detector 400 having a detector of alpha particles 410 of an integrated type may be formed as illustrated in FIGS. 24A and 24B, starting, for example, from an SOI (Silicon-On-Insulator) substrate. In this case, the substrate 405 comprises a first semiconductor layer 406 with conductivity of, e.g., of a P type, an insulating layer 407, and a second semiconductor layer 408, which also has conductivity, e.g., of a P type. A first and second wells 412, 413, for example of an N type are formed, via known processes, in the second semiconductor layer 408. The first well 412 may be annulus-shaped and may surround the first well 412, delimiting with the latter an annular portion 414, of a P type like the substrate, as may be seen in FIG. 23. The first well 412 is further insulated from the rest of the substrate 408 and from possible other components, for example, by insulation regions (not illustrated), in a per se known manner. The sample chamber 4 is obtained with a masking and etching process, by removing part of the first well 413.

Next, in a way not illustrated, the alpha-particle detector 410 is connected to the other components of the gas detector 400 via electrodes (for example, of tungsten) arranged at the top and possibly at the sides, for example on the walls of the detection chamber 4A. In particular, the alpha-particle detector 410 may have a common electrode (not illustrated) in contact with the P-type areas 414 and two electrodes in contact with the N-type wells 412, 413

Then the first and second protective layers 3A, 3B and the grids 53, 54 are formed, as illustrated in FIG. 24B.

Finally the thermoelectric device 56 and the heat dissipator 57 are fixed. Alternatively, the first protective layer 3A may be replaced by a further perforated substrate, on which the cooling grid 54 has already been formed.

To increase the detection efficiency, it is possible to provide a plurality of sample chambers 4 arranged side by side, as illustrated in FIG. 25. The sample chambers 4 may have a dimension much greater than the other. In this way, it is possible to obtain measuring times shorter than one hour, for example just a few minutes, or even less, according to the environmental concentration, with dimensions of the detector, for example, of some centimeters or less, down to a few millimeters.

Finally, it is clear that modifications and variations may be made to the detector and to the optical system described and illustrated herein, without thereby departing from the scope of the present invention, as defined in the attached claims.

For instance, in the embodiments, it is possible to stack on top of one another different substrates having respective cavities arranged on top of one another that together form a single larger sample chamber for increasing the sampling volume.

In some embodiments, the sample chamber 4 may not be a through chamber, and it is possible to reverse the polarities of the grids 10 and 11 to cause air ejection or to reverse the flow. Likewise, it is also possible to obtain reversal of the flow and emptying of the sample chamber 4 in the case of the heat pump illustrated in FIGS. 13 and 23, if all the grids 53, 54 may be heated and are in thermal contact with a respective Peltier cell.

If the body 2 is provided with a number of substrates arranged on top of one another, it is possible to provide one or more intermediate biased grids to increase the pumping efficiency.

The shape of the sample chamber 4 may also be modified as desired, using selective silicon etching techniques.

Arranging a number of substrates on top of one another, it is possible to obtain two or more optical systems 5, 6 with different heights of the sample chamber 4, if desired, for increasing the accuracy of the measurements.

In case of a vertical sample chamber, the air inlet and outlet openings and thus, in the case of an ionic pump 50, the grids 10 and 11, i.e., the heating and cooling elements 51, 52, may not be aligned with one another. Furthermore, in the case of horizontal sample chambers, the air inlet and outlet openings and thus, in the case of the ionic pump 50, the grids 10 and 11, i.e., the heating and cooling elements 51, 52, may be arranged on opposite faces 2A, 2B of the body 2. The various parts that make up the described detector may be formed separately in different integrated circuits and assembled to form encapsulated systems SIPs having equivalent functions.

In particular illustrative embodiments, the protective layers 3A, 3B may be replaced by respective further substrates of semiconductor material, where further integrated circuits may possibly be accommodated.

The alpha-particle detector 310 of FIG. 22 may be formed, as an alternative to what is illustrated in the enlarged detail, as described with reference to FIGS. 23, 24B.

The invention claimed is:

1. A detection device comprising:
   a body of semiconductor material having a first face and a second face;
   a cavity comprising a first end and an opposite second end;
   a detection area in the cavity;
   a concentration area in the cavity, the concentration area being coupled to the detection area, the concentration area comprising a wider cross-sectional footprint than the detection area;
   a gas pump integrated in the body and configured to force a movement of gas from the concentration area through the cavity towards the detection area, the gas pump comprising a first grid at the first end and a second grid at the second end; and
   a detection system arranged at least in part in the detection area.

2. The detection device according to claim 1, wherein the gas pump is of an ionic type and comprises an ionization structure arranged on a first side of the detection area and an attracting structure arranged on a second side of the detection area, the ionization structure and the attracting structure configured to ionize gas entering the cavity and force the gas through the detection area.

3. The detection device according to claim 2, wherein the first grid comprises a conductive grid having tips, and the second grid comprises a biasable conductive grid.

4. The detection device according to claim 1, wherein the gas pump is of a thermal type and comprises a heating structure arranged on a first side of the detection area and a cooling structure arranged on a second side of the detection area, the heating structure and the cooling structure being configured to generate a temperature difference and gas movement through the detection area.

5. The detection device according to claim 4, wherein the heating structure comprises a conductive grid configured to generate heat by Joule effect, and the cooling structure comprises a Peltier cell.

6. The detection device according to claim 1, wherein the cavity is a through cavity and extends between the first and second faces, and the gas pump is configured to generate gas movement through the body.

7. The detection device according to claim 1, wherein the cavity extends generally parallel to the first face and has inlet and outlet openings on the body, and the gas pump is configured to generate gas movement in a generally parallel direction through the body.

8. The detection device according to claim 1, wherein the detection system comprises an optical system and comprises a light source configured to generate an optical beam, and a photodetector configured to detect scattered light, the optical system configured to direct the optical beam towards the detection area.

9. The detection device according to claim 8, wherein the light source comprises a laser source integrated in the body in a first position adjacent to the detection area, and the photodetector is integrated in the body in a second position adjacent to the detection area.

10. The detection device according to claim 9, wherein the optical system comprises a beam adjustment assembly arranged between the light source and the detection area, the beam adjustment assembly including a plurality of lenses and a hydrophobic support or a variable hydrophobicity support carrying the plurality of lenses.

11. The detection device according to claim 8, wherein the light source is configured to generate polarized laser light.

12. The detection device according to claim 8, wherein the light source is configured to generate polarized laser light, and the photodetector comprises a polarization-splitting unit and two pluralities of photoreceiver elements, each plurality of photoreceiver elements configured to detect light having a single respective polarization.

13. The detection device according to claim 12, wherein the polarization-splitting unit comprises a grating coupler.

14. The detection device according to claim 8, wherein the detection area has oblique walls having reflecting surfaces configured to define an optical path of the optical beam, the light source and the photodetector being arranged in facing positions of the detection area on the optical path.

15. The detection device according to claim 1, wherein the detection system comprises an alpha-particle detector.

16. The detection device according to claim 15, wherein the alpha-particle detector comprises a semiconductor substrate having a portion extending through the cavity and comprising an array of sensitive regions and a plurality of through holes adjacent to the sensitive regions, wherein attraction electrodes are formed on walls of the plurality of through holes.

17. The detection device according to claim 15, wherein the alpha-particle detector is integrated in the body of semiconductor material on walls delimiting the cavity.

18. A method for detecting particles comprising:
providing a cavity in a semiconductor body, the cavity comprising a detection area, a concentration area, a first end and an opposite second end, the concentration area being coupled to the detection area, wherein the concentration area comprises a wider cross-sectional footprint than the detection area;
generating gas movement from the concentration area to the detection area of the cavity of the semiconductor body via a gas pump, the gas pump comprising a first grid at the first end and a second grid at the second end; and
measuring a particle parameter within the detection area via a detection device.

19. The method according to claim 18, wherein generating the gas movement comprises generating ionized gas molecules in proximity of the first end of the detection area and attracting the ionized gas molecules towards the second end of the detection area, wherein the generating the ionized gas and the attracting generates a movement of the gas molecules through the detection area and increasing a particle concentration within the detection area.

20. The method according to claim 18, wherein generating the gas movement comprises generating a thermal gradient in the detection area, wherein the thermal gradient generates a movement of gas molecules in the gas through the detection area and increasing a particle concentration within the detection area.

21. The method according to claim 18, wherein the particle parameter comprising one of a number and size distribution of the particles.

22. A detection device comprising:
a body of semiconductor material having a first major surface, a second major surface, and a cavity;
a detection area in the cavity;
a gas pump integrated in the body and configured to force a movement of gas through the cavity towards the detection area; and
a detection system in the detection area, the detection system comprises an optical system, a light source, and a photodetector, wherein the optical system comprises a beam adjustment assembly arranged between the light source and the detection area, the beam adjustment assembly including a plurality of lenses and a hydrophobic support or a variable hydrophobicity support carrying the plurality of lenses.

23. The detection device according to claim 22, further comprising:
a first conductive grid disposed at the first major surface; and
a second conductive grid disposed at the second major surface, the cavity extending between the first conductive grid and the second conductive grid.

24. The detection device according to claim 22, further comprising:
a heating element disposed at the first major surface; and
a cooling element disposed at the second major surface, the cavity extending between the heating element and the cooling element.

25. A particle detecting device comprising:
a semiconductor body having a first major surface, a second major surface;
a cavity comprising a first end and an opposite second end;
a detection area disposed in the cavity, the detection area extending from the first end;
a concentration area disposed in the cavity extending from the second end towards the detection area, the concentration comprising a wider footprint than the detection area;
a gas pump disposed in the body and comprising a first grid at the first end and a second grid at the second end; and
an optical particle detection system disposed in the semiconductor body, the optical particle detection system comprising a light source disposed at a first sidewall of the detection area and a photodetector disposed at a second sidewall of the detection area, the first sidewall facing the second sidewall.

26. The particle detecting device according to claim 25, wherein the optical particle detection system comprises a beam adjustment assembly arranged between the light source and the detection area, the beam adjustment assembly including a plurality of lenses.

27. The particle detecting device according to claim 26, wherein the plurality of lenses comprises a first lens having a first refractive index disposed in a transparent material having a second refractive index and a second lens having a third refractive index, wherein the second refractive index is different from the first and the third refractive indices.

28. The particle detecting device according to claim 27, wherein the second refractive index is smaller than the third refractive index, wherein the third refractive index is smaller than the first refractive index.

29. The particle detecting device according to claim 27, wherein the first lens is disposed on a first hydrophobic surface and the second lens is disposed on a second hydrophobic surface, wherein the hydrophobicity of the first hydrophobic surface is different from the hydrophobicity of the second hydrophobic surface.

30. The particle detecting device according to claim 27, wherein the first lens and the second lens comprise convergent lenses.

31. The particle detecting device according to claim 25, wherein the light source comprises a plurality of emitting photodiodes and wherein the photodetector comprises a plurality of receiving photodiodes.

32. The particle detecting device according to claim 25, wherein the first grid comprises a pair of electrodes configured to be coupled between a potential difference.

33. The particle detecting device according to claim 25, wherein the first grid comprises a heating element and the second grid is coupled to a cooling element.

34. The particle detecting device according to claim 25, further comprising a second light source disposed at a third sidewall of the detection area orthogonal to the first sidewall and a second photodetector disposed at a fourth sidewall of the detection area orthogonal to the second sidewall.

35. The particle detecting device according to claim 25, wherein the first and the second ends of the gas pump are disposed at the first major surface.

36. The particle detecting device according to claim 25, wherein the first end of the gas pump is disposed at the first major surface and the second end of the gas pump is disposed at the second major surface.

37. The particle detecting device according to claim 25, further comprising a first plurality of holes at the first major surface and a second plurality of holes at the second major surface.

38. The particle detecting device according to claim 25, wherein the semiconductor body comprises a first substrate having the first major surface and a second substrate having the second major surface.

* * * * *